United States Patent [19]

von Daehne et al.

[11] 4,100,276
[45] Jul. 11, 1978

[54] FUSIDIC ACID DERIVATIVES

[75] Inventors: Welf von Daehne, Rungsted Kyst; Poul Rodbroe Rasmussen, Frederikssund, both of Denmark

[73] Assignee: Leo Pharmaceutical Products Ltd. A/S, Ballerup, Denmark

[21] Appl. No.: 744,978

[22] Filed: Nov. 24, 1976

[30] Foreign Application Priority Data

Dec. 3, 1975 [GB] United Kingdom ............... 49714/75
Apr. 20, 1976 [GB] United Kingdom ............... 16015/76

[51] Int. Cl.² .......................... A61K 31/56; C07J 9/00
[52] U.S. Cl. .................... 424/238; 260/239.5; 260/239.55; 260/397.1; 424/242
[58] Field of Search .....................................
/Machine Searched Steroids; 260/397.1, 239.5

[56] References Cited

U.S. PATENT DOCUMENTS 3,867,413  2/1975  von Daehne et al. ............ 260/397.1
4,004,004  1/1977  von Daehne et al. ............ 260/397.1

*Primary Examiner*—Elbert L. Roberts
*Attorney, Agent, or Firm*—Cushman, Darby & Cushman

[57] ABSTRACT

The invention relates to a new series of fusidic acid derivatives, to salts and easily hydrolyzable esters thereof, to the preparation of these compounds and to pharmaceutical compositions containing the compounds, the new compounds having the general formula:

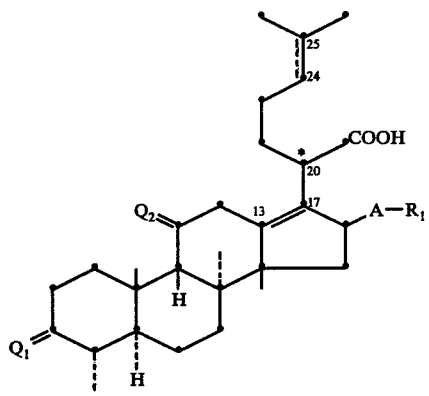

in which $Q_1$ and $Q_2$ stand for the group

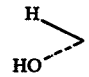

or oxygen, A represents oxygen or sulphur, and $R_1$ stands for a straight or branched alkyl radical having from 1 to 12 carbon atoms, $R_1$ can further be an alkenyl or alkynyl radical having from 3 to 6 carbon atoms, a cycloalkyl radical having from 3 to 7 carbon atoms in the alicyclic ring, an aralkyl or aryl radical, $R_1$ can also be a heterocyclic radical having 5 or 6 ring atoms and containing oxygen, sulphur and/or nitrogen atoms, $R_1$ optionally being further substituted, and in which formula I the dotted line between C-24 and C-25 indicates that the carbon atoms in question are connected by either a double bond or a single bond, and the asterix at C-20 indicates that the compounds exist in two diastereomeric forms, and thus the invention comprises the pure diastereomers as well as mixtures of these.

The compounds of the present invention possess antibacterial properties and show further interesting antimicrobial and pharmacokinetic properties.

53 Claims, No Drawings

FUSIDIC ACID DERIVATIVES

The present invention relates to a new series of fusidic acid derivatives, to salts and easily hydrolysable esters thereof, to the preparation of these compounds and to pharmaceutical compositions containing the compounds. The new compounds have the general formula:

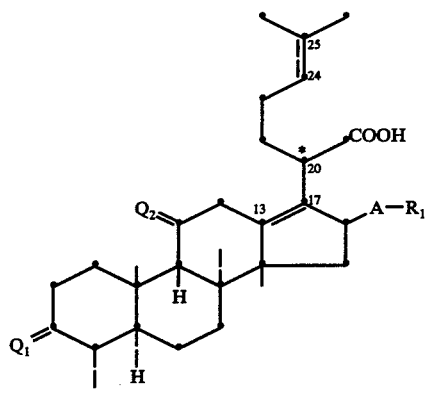

in which $Q_1$ and $Q_2$ stand for the group

or oxygen, A represents oxygen or sulphur, and $R_1$ stands for a straight or branched alkyl radical having from 1 to 12 carbon atoms, such as methyl, ethyl, propyl, isopropyl, butyl, isobutyl, tert.butyl, the known isomers of pentyl, hexyl, heptyl, octyl and dodecyl, such alkyl radicals being optionally substituted with halogen atoms or hydroxy, alkyloxy, aralkyloxy, aryloxy, alkanoyloxy, aralkanoyloxy, arolyoxy, sulfhydryl, alkylthio, aralkylthio, arylthio, alkanoylthio, aroylthio, azido, nitro, cyano, thiocyano, hydroxycarbonyl, alkyloxycarbonyl, aryloxycarbonyl, amino, alkylamino, dialkylamino, arylamino, alkanoylamino, and aroylamino groups; $R_1$ can further be an alkenyl or alkynyl radical having from 3 to 6 carbon atoms, such as allyl, crotyl or propargyl, a cycloalkyl radical having from 3 to 7 carbon atoms in the alicyclic ring, such as cyclopropyl, cyclobutyl, cyclopentyl, cyclohexyl, cycloheptyl, or the mono- or dihalo, lower alkyl, lower alkoxy or hydroxy substituted analogues, an aralkyl or aryl radical, such as benzyl, phenylethyl, phenyl, furfuryl or naphthyl, optionally substituted with halogen, lower alkyl, hydroxy or alkoxy radicals; $R_1$ can also be a heterocyclic radical having 5 to 6 ring atoms and containing oxygen, sulphur and/or nitrogen atoms, such as 2-or 3-pyrrolyl, 2- or 3-furyl, 2- or 3-thienyl, 2-, 3- or 4-pyridyl, 2-, 4- or 5-pyrimidinyl, 2- or 3-pyrazolyl, imidazolyl e.g. 1-methyl-2-imidazolyl, triazolyl, e.g. 5-methyl-1,2,4-triazol-3-yl, tetrazolyl e.g. 1-methyl-1H-tetrazol-5-yl, thiazolyl, thiadiazolyl e.g. 5-methyl-1,3,4-thiadiazol-2-yl.

In formula I the dotted line between C-24 and C-25 indicates that the carbon atoms in question are connected by either a double bond or a single bond, and the asterix at C-20 indicates that the compounds exist in two diastereomeric forms. The invention comprises the pure diastereomers as well as mixtures of these.

Where not otherwise stated the term alkyl in the radicals mentioned above stands for a $C_1$ to $C_4$ alkyl radical.

The compounds of formula I can be used as such or in the form of salts or easily hydrolysable esters. The salts of the compounds are especially the pharmaceutically acceptable, non-toxic salts, such as alkali metal salts and alkaline earth metal salts, for example sodium, potassium, magnesium or calcium salts, as well as salts with ammonia or suitable non-toxic amines, e.g. lower alkyl amines for example triethylamine, hydroxy-lower alkylamines, for example 2-hydroxyethylamine, bis-(2-hydroxyethyl)-amine or tri-(2-hydroxyethyl)-amine, cycloalkylamines, for example dicyclohexylamine, or benzylamines, for example N,N'-dibenzyl-ethylenediamine or dibenzylamine.

For certain purposes also the silver salts of the compounds may be used, especially for topical treatment.

The easily hydrolysable esters can e.g be alkanoyloxyalkyl, aralkanoyloxyalkyl, aroyloxyalkyl esters, such as acetoxymethyl, pivaloyloxymethyl, benzoyloxymethyl esters, and the corresponding 1'-oxyethyl derivatives, or alkoxycarbonyloxyalkyl esters, such as methoxycarbonyloxymethyl, ethoxycarbonyloxymethyl and the corresponding 1'-oxyethyl derivatives, or lactonyl esters, such as phthalidyl esters, or dialkylaminoalkyl esters, such as diethylaminoethyl esters.

The antibacterial properties of fusidic acid and some newer fusidic acid derivatives against a number of gram-positive bacteria are well known (J.Med.Chem. 9, 15 (1966) and U.S. Patent Application No. 693,976.

Furthermore another type of fusidic acid derivatives are known to exhibit a more bactericidal effect that these, but against a more limited number of bacteria (U.S. Pat. No. 3,499,012).

Now, however, it has been found that the compounds of the present invention possess antibacterial properties which combine the bactericidal effect of the latter type of derivatives with the broader antibacterial spectrum of the former type of derivatives, and show further interesting antimicrobial and pharmacokinetic properties, both in vivo and in vitro. Thereby the compounds of the invention can be used in the treatment of bacterial infections in humans and animals both systemically and topically.

In vitro investigations have for instance shown that the compounds are highly potent against a number of bacteria e.g. staphylococci, streptococci, corynebacteriae, bacteroides species, and Bacillus subtilis. In table A below the in vitro activity of some of the compounds of the invention against a number of pathogenic organisms is shown. It can be seen that the compounds of the invention have the same strong activity against a fusidic acid resistant strain of Staph, aureus as against a fusidic acid sensitive variant of the same strain. This clearly shows that there is no cross resistance between fusidic acid and the compounds of the invention. Although less active against fusidic acid sensitive staphylococci than fusidic acid, the compounds of the invention show a similar or even better activity against streptococci, Bacteroides fragilis and Corynebacterium acnes when compared with fusidic acid.

Table A:

| Organisms | Concentration required for 50% inhibition ($IC_{50}$) in μg/ml | | | | | | | | | | | |
|---|---|---|---|---|---|---|---|---|---|---|---|---|
| | Ex. 1 | Ex. 2 | Ex. 8 | Ex. 11 | Ex. 13 | Ex. 14 | Ex. 23 | Ex. 26 | Ex. 27 | Ex. 31C | Ex. 31D | Fusidic acid |
| Streptococcus pyogenes Leo EC | 0.5 | 0.2 | 0.5 | 1.6 | 0.63 | 0.32 | 0.63 | 0.5 | 0.63 | 0.5 | 0.63 | 0.63 |
| Streptococcus sp. Leo EG2 | 1.6 | 0.5 | 0.5 | 1.6 | 1.6 | 1.6 | 1.6 | 0.5 | 1.0 | 0.63 | 0.79 | 1.6 |
| Staphylococcus aureus Leo CC178B | 1.6 | 6.3 | 2 | 2.7 | 1.6 | 1.6 | 1.6 | 1.6 | 1.6 | 1.6 | 1.6 | 0.025 |
| Staph. aureus, Leo CC178H$_2$ (fusidic acid resistant strain) | 1.6 | 10 | 2.5 | 3.2 | 1.6 | 1.6 | 1.6 | 1.6 | 1.6 | 1.6 | 1.6 | 32 |
| Staph. aureus Leo CJ145 | 3.2 | 100 | | 3.2 | 7.9 | 5.0 | 7.9 | | 4.0 | 4.0 | 5.0 | 16 |
| Bacteroides fragilis, Leo JA2 | 20 | 13 | >100 | 2 | 2 | 4 | 16 | 20 | 10 | 6.3 | | 1.6 |
| Corynebact. acnes Leo FN | 0.5 | 0.63 | 1.6 | 2 | 0.5 | 1.6 | 0.79 | 0.5 | 0.63 | 0.63 | 1.6 | 0.2 |

In vitro investigations have further shown that the antibacterial effect of the compounds is highly bactericidal even under conditions where the effect of fusidic acid is solely bacteriostatic. Furthermore, it has been found that combinations consisting of one or more of the compounds of the invention and fusidic acid or orher fusidic acid derivatives, such as dihydrofusidic acid and compounds of our copending U.S. patent application Ser. No. 693,976 show an effect exceeding the additive effect of the single components. Also, by use of such a combination the development of resistance against each of the components can be prevented.

Furthermore, the compounds of the invention are chemically more stable than fusidic acid, a fact which is of practical importance, e.g. in the preparation of formulations for topical use. Like fusidic acid they are absorbed efficiently from the gastro-intestinal tract and are practically non-toxic.

The compounds of formula I can be prepared by a method comprising a first step in which an intermediate of the general formula II is formed.

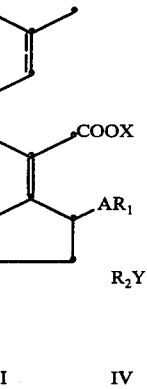

II

In formula II $Q_1'$ stands for $Q_1$ as defined above or for

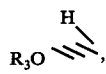

$R_3$ representing an alkanoyl, an aralkanoyl or an aroyl radical; $R_1$, A, $Q_2$ and the dotted line between C-24 and C-25 have the meaning as defined above; $R_2$ represents a benzyl radical or a substituted benzyl radical, such as p-nitrobenzyl or p-methoxybenzyl radical.

The compounds of formula II can be prepared according to one of the following methods:

A. A compound of the general formula III is reacted with a compound of the general formula IV to give a compound of the general formula II:

III    IV

In these formulae $Q_1'$, $Q_2$, $R_1$, A, $R_2$ and the dotted line between C-24 and C-25 have the meaning as defined above, X stands for hydrogen or a cation, such as Na$^+$, K$^+$, Ag$^+$, an ammonium, or trialkylammonium ion, and Y is a chlorine, bromine or an iodine atom. The reaction is performed in an inert organic solvent, e.g. dimethylformamide, and at room temperature or at slightly elevated temperature.

B. A compound of the general formula V is reacted with a compound of the general formula VI to form a compound of formula II.

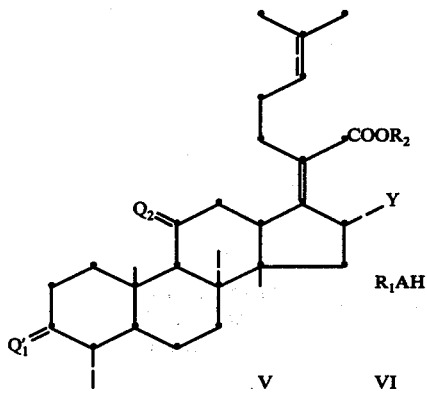

V    VI

In these formulae $Q_1'$, $Q_2$, $R_2$, Y, $R_1$, A and the dotted line between C-24 and C-25 have the meaning as defined above. If A in formulae II and VI represents oxygen, the reacting compounds of formula VI may preferably be used as solvents, and the reaction is performed in the presence of a silver or mercury salt, e.g. silver carbonate, silver trifluoroacetate or mercuric acetate, or a base, e.g. potassium carbonate, sodium carbonate or sodium alcoholate, and at room temperature or at slightly elevated temperature. If A in formulae II and VI stands for sulphur, the reaction is performed in an inert organic solvent, preferably ethanol, dimethylsulfoxide or dimethylformamide, in the presence of a base, e.g. sodium or potassium hydroxide or sodium hydride, and at or below room temperature or at slightly elevated temperature.

C. Compounds of the general formula II, in which A stands for sulphur and $R_1$ is aryl or aromatic heterocyclyl, can be prepared by reacting a compound of the general formula V, in which Y stands for a hydroxyl group, with a phosphine, e.g. tributylphosphine or triphenylphosphine, and a compound of the general formula $R_1SSR_1$. The reaction is performed either without a solvent or in an inert organic solvent, preferably dimethylformamide or pyridine, at or below room temperature.

The preparation of the starting compounds of formulae III and V is described in our co-pending U.S. patent application Ser. No. 693,976 in which application also methods are given for the preparation of the intermediate compounds of formula II.

In a final step the compounds of formula II are converted into the compounds of formula I or salts thereof by reaction with a base, such as aqueous sodium or potassium hydroxide, sodium hydride or potassium tert. butylate, in the presence of an organic solvent.

If this solvent is dimethylsulfoxide, the reaction proceeds especially rapidly and gives outstanding yields of the pure compounds. This is probably due to the formation of the carbanion

when this solvent is brought into contact with a base. This ion, acting as an extraordinary soft base, catalyses the isomerisation of the double bond, thus giving rise to the formation of compounds of formula I (with a double bond between C-13 and C-17) instead of compounds of formula III (with a double bond between C-17 and C-20), which are the major products when other solvents are used, as described in out co-pending U.S. patent application Ser. No. 693,976.

Compounds of the invention containing a single bond between C-24 and C-25 can also be prepared from the corresponding unsaturated analogues by reduction, e.g. a catalytic hydrogenation using, for instance, palladium on carbon as a catalyst.

The compounds of the invention, in which $Q_1$ and/or $Q_2$ stand for an oxygen atom, can also be prepared from the corresponding compounds, in which $Q_1$ and $Q_2$ stand for

by a suitable oxydation process.

The easily hydrolysable esters of the compounds of formula I can be prepared in known manner by methods described in the literature.

The compounds of the invention prepared according to these methods consist of mixtures of the two possible C-20-isomers. These mixtures can be separated into the two pure isomers by conventional methods, e.g. fractionate crystallization or chromatographic procedures.

It is a further object of the present invention to provide pharmaceutical compositions which are useful in the treatment of infectious diseases in the human and veterinary practice.

With this object in view, the compositions of the invention contain as an active component at least one member selected from the group consisting of compounds of formula I, salts thereof with non-toxic, pharamceutically acceptable bases, and easily hydrolysable esters thereof, together with solid or liquid pharmaceutical carriers and/or diluents.

In the said compositions, the proportion of therapeutically active material to carrier substance can vary between 1% and 95% by weight. The compositions can be worked up to various pharmaceutical forms of presentation, such as granulate, tablets, pills, dragees, suppositories, capsules, sustained-release tablets, suspensions, injection medicine, or so far as mixtures are concerned, they may be filled in bottles or tubes or similar containers. Pharmaceutical organic or inorganic, solid or liquid carriers and/or diluents suitable for oral, enteral, parenteral or topical administration can be used to make up compositions containing the present compounds. Water, gelatine, lactose, starch, magnesium stearate, talc, vegetable and animal oils and fats, benzyl alcohol, gum, polyalkylene glycol, petroleum jelly, cocoa butter, lanolin or other known carriers for medicaments are all suitable, while stabilizing agents, wetting and emulsifying agents, salts for varying the osmotic pressure or buffers for securing an adequate pH-value of the composition can be used as auxiliary agents.

Furthermore, the composition may contain other pharmaceutically active components which can appropriately be administered together with the compounds of the invention in the treatment of infectious diseases, such as other suitable antibiotics, in particular such antibiotics, which may enhance the activity and/or prevent development of resistance. Such antibiotics include fusidic acid and other fusidic acid derivatives, β-lactam antibiotics, tetracyclines, rifamycins, erythromycin, lincomycin, and clindamycin. Other compounds which advantageously may be combined with the compounds of the invention, especially in topical preparations, include e.g. corticosteroids, like hydrocortisone, triamcinolone or fluocinolone.

For granulates, tablets, capsules or dragees the pharmaceutical composition of the invention appropriately contains from 25 percent to 95 percent of the active substance of the invention, and in oral suspensions the corresponding amount is appropriately from 2–25 percent.

For parenteral use the compounds of the invention are preferably given by injection of pharmaceutical compositions containing from 1 to 20 percent of the active ingredient.

When the compounds of formula I are administered in the form of salts with pharmaceutically acceptable, non-toxic bases, the preferred salts are for instance the sodium salts or the diethanolamine salts, but other pharmaceutically acceptable and non-toxic salts may be used.

As indicated above, the compounds of formula I, their salts and easily hydrolysable esters may be worked up to pharmaceutical forms of presentation including suspensions, powders, ointments and creams. A pharmaceutical preparation for oral treatment may also be in the form of a suspension containing either a compound of formula I or a sparingly soluble salt thereof with a pharmaceutically acceptable base or an easily hydrolysable ester thereof in an amount of from 20 to 100 mg per ml of vehicle. A pharmaceutical preparation for topical treatment may be in the form of a powder, an ointment or a cream containing a compound of the invention in an amount of from 0.5 to 10 g per 100 g of preparation.

Another object of the invention resides in the selection of a dose of the compounds of the invention which dose can be administered so that the desired activity is achieved without simultaneous secondary effects. In the human therapy, the compounds of the invention are conveniently administered (to adults) in dosage units containing not less than 50 mg and up to 1000 mg, preferably from 250 to 750 mg, calculated as a compound of formula I.

By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents or carriers.

In the form of a dosage unit, the compound may be administered once or more times a day at appropriate intervals, always depending, however, on the condition of the patient, and in accordance with the prescription made by the medical practitioner.

Thus in systemic treatment a daily dose will be from 0.25 g to 4 g per day, preferably an amount of from 0.5 to 3 g, calculated as a compound of formula I.

By the term "dosage unit" is in connection with the topical use meant a unitary, i.e. a single dose capable of being administered topically to the patients and applicating per sq. centimeter of the infected area from 0.1 mg to 10 mg and preferably from 0.2 mg to 1 mg of the compound in question.

If the composition is to be injected, a sealed ampoule, a vial or a similar container may be provided containing a parenterally acceptable aqueous or oily injectable solution or dispersion of the active material as the dosage unit.

The parenteral preparations are in particular useful in the treatment of conditions in which a quick response to the treatment is desirable. In the continuous therapy of patients suffering from infectious diseases, the tablets or capsules may be the appropriate form of pharmaceutical preparation owing to the prolonged effect obtained when the drug is given orally, in particular in the form of sustained-release tablets.

In the treatment of infectious diseases, such tablets may advantageously contain other active components, as mentioned hereinbefore.

Still another object of the invention is to provide a method of treating patients suffering from infectious diseases, the method comprising administering to patients from 0.25 g to 4 g per day, preferably from 0.5 to 3 g per day, calculated as a compound of the formula I, or an equivalent amount of a salt or an ester as defined before of a compound of the formula I. Preferably, the compound is given in the form of the dosage units aforesaid.

The invention will be further described in the following Examples which are not to be construed as limiting the invention.

EXAMPLE 1

3α,11α-Dihydroxy-16β-phenylthiofusida-13(17), 24-dien-21-oic acid sodium salt

To an icecooled solution of 3 -acetyl-16-epideacetyl-fusidic acid benzyl ester (15 g; 25 mmol) and diphenyl-disulfide (13.5 g, 62 mmol) in dry pyridine (100 ml) was added tributylphosphine (30 mll 126 mmol), and the mixture was left at 5° C. After 3 days, additional amounts of diphenyldisulfide (3.4 g, 16 mmol) and tributylphosphine (7.5 ml; 31.5 mmol) were added, and after a total period of 5 days at 5° C a mixture of dimethylsulfoxide (100 ml) and 30 per cent aqueous sodium hydroxide (50 ml) was added, and the resulting suspension was heated to 70° C for 3 hours. After cooling to 20° C, ether (1 litre), water (3 litre), and saturated aqueous sodium chloride (100 ml) was then added with stirring causing the desired product to precipitate as colourless crystals. After 1 hour of stirring, the organic phase containing the crystals was filtered, and the crystals were washed with water (100 ml) and ether (200 ml), and dried to yield 3α,11α-dihydroxy-16β-phenylthiofusida13(17), 24-dien-21-oic acid sodium salt as a mixture of the two C-20-isomers; melting point 243°–247° C.

Found: C 63.65, H 8.62, S 4.84, H$_2$O 10.4% C$_{35}$H$_{49}$NaO$_4$S, 4H$_2$0. Requires: C 63.59, H 8.69, S 4.85, H$_2$O 10.9%.

EXAMPLE 2

The sodium salt of 3α,11α-dihydroxy16β-(4'-bromophenylthio)fusida-13(17),24-dien-21-oic acid Following the procedure of Example 1 and substituting di-(4-bromophenyl)disulfide for diphenyldisulfide, 3α,11α-dihydroxy-16β--(4'-bromophenylthio)fusida-13(17),24 -dien-21-oic acid sodium salt was obtained as a mixture of the two C-20-isomers; melting point 231°–239° C.

Found: C 61.67, H 7.63, S 4.83, Br 11.24% C$_{35}$H$_{48}$NaBrO$_4$S, H$_2$O. requires: C 61.30, H 7.35, S 4.68, Br 11.66%,

EXAMPLE 3

The sodium salt of 3α,11α-dihydroxy-16β-(2′,5′-dichlorophenylthio)-fusida-13(17), 24-dien-21-oic acid Following the procedure of Example 1 and substituting di(2,5-dichlorophenyl)disulfide for diphenyldisulfide, 3α,11α-dihydroxy-16β-(2′,5′-dichlorophenylthio)-fusida-13(17), 24-dien-21oic acid sodium salt was prepared, as a crystalline product with no well-defined melting point. (The product is a mixture of the two C-20-isomers).

EXAMPLE 4

The sodium salt of 3α,11α-dihydroxy-16β-phenylthiofusida-13(17), 24-dien-21-oic acid 16-Dpideacetylfusidic acid benzyl ester (3 g, 5.3 mmol) and diphenyldisulfide (4.9 g, 23 mmol) were dissolved in pyridine (20 ml), the solution was cooled to 0°0 C, and tributylhosphine (5.5 ml, 23 mmol) was added. After standing at 20° C for 3 days, the solution was diluted with ether (100 ml), washed with 4 N hydrochloric acid (2 × 25 ml), with 2 N sodium hydroxide (2 × 25 ml) and with water (2 × 50 ml), dried, and evaporated in vacuo to yield crude 16-deacetoxy-16β-phenylthiofusidic acid benzyl ester as an oil. This residue was dissolved in a mixture of dimetylsulfoxide (200 ml) and 2 N aqueous sodium hydroxide (50 ml). After heating for 3 hours at 70° C ether (100 ml) and water (200 ml) was slowly added to the reaction mixture to precipitate the desired product as colourless crystals. The ethereal phase, containing the crystals, was filtered, and the crystals were washed with water and ether, and dried to afford the sodium salt of 3α,11α-dihydroxy-16β-phenylthiofusida-13(17), 24-dien-21-oic acid in the form of a mixture of the two C-20-isomers; melting point 243°–247° C.

EXAMPLES 5-7

Following the procedure of Example 4 and substituting the disulfides listed in table I for diphenyldisulfide, the 16β-thioethers of 3α,11α-dihydroxyfusida-13(17),24-dien-21-oic acid sodium salt in table I were prepared as mixtures of the two C-20-isomers.

Table I:

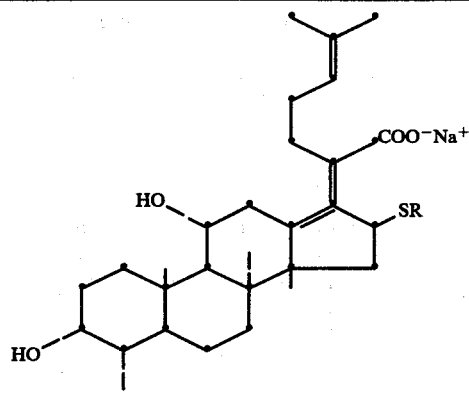

| Example | Disulfide | Resulting compound R | Mp (° C) |
|---|---|---|---|
| 5 | Di(o-methylphenyl) | o-CH₃.C₆H₄ | 222–238 |
| 6 | Di(m-methylphenyl) | m-CH₃C₆H₄ | 226–234 |

Table I:-continued

| Example | Disulfide | Resulting compound R | Mp (° C) |
|---|---|---|---|
| 7 | Di(p-methylphenyl) | p-CH₃C₆H₄ | 199–213 |

EXAMPLE 8

3α,11α-Dihydroxy-16β-phenylthiofusida-13(17)-en-21-oic acid, sodium salt.

To an icecooled mixture of 16-epideacetyl-24,25-dihydrofusidic acid benzyl ester (6.2 g, 11 mmol) and diphenyldisulfide (6.3 g, 29 mmol) was added tributylphosphine (14 ml, 59 mmol), and the mixture was left at 20° C for 48 hours. 40 ml of dimethylsulfoxide and 20 ml of 30 per cent aqueous sodium hydroxide were then added, and the resulting suspension was heated to 70° C for two hours. After cooling to 20° C, ethyl ether (200 ml) and water (600 ml) were added. After some hours the desired product precipitated as colourless crystals. After 24 hours at room temperature, the organic phase containing the crystals was filtered, and the crystals were washed with water (100 ml) and ethyl ether (100 ml), and dried to yield the sodium salt of 3α,11α-dihydroxy-16β-phenyltiofusida-13(17)-en-21-oic acid as a mixture of the two C-20-isomers. This crude product was recrystalized from methanol-water giving the analytically pure compound; melting point 235°–241° C.

EXAMPLE 9

The sodium salt of 3α,11α-dihydroxy-16β-isopropylthiofusida-13(17),24-dien-21-oic acid To a solution of potassium hydroxide (10 g; 150 mmol) and isopropyl morcaptan (30 ml; 320 mmol) in pure ethanol (750 ml) and added 3-acetyl-16-deacetoxy-16α-bromofusidic acid benzyl ester (24 g; 36 mmol), and the resulting solution was left at room temperature for 3 days. Thereafter, the major part of ethanol was removed in vacuo, and to the residue was added ethyl acetate (200 ml) and water (100 ml). The organic phase was separated, washed twice with water, dried, and evaporated in vacuo to yield crude 3-acetyl-16-deacetoxy-16β-isopropylthiofusidic acid benzyl ester as an oily residue.

This residue was disslved in a mixture of 30 percent aqueous sodium hydroxide (40 ml) and dimethylsulfoxide (200 ml). After heating for 3 hours at 70° C, water (1000 ml) and ether (200 ml) was added with stirring. After 1 hour, the organic phase containing the desired product as colourless crystals was separated, the crystals were filtered off, washed with water and ether, and dried to yield 3α,11α-dihydroxy-16β-isopropylthiofusida-13(17), 24-dien-21-oic acid sodium salt as a mixture of the two C-20-isomers.

Recrystallization from methanol-water gave the analytical sample, melting point 220°–228° C.

Found: C 61.68, H 9.32, S 5.14% $C_{32}H_{51}O_4SNa$, $4H_2O$, requires: C 61.31, H 9.49, S 5.12%.

EXAMPLES 10–24

16β-Thioethers of 3α,11α-dihydroxy-fusida-13(17), 24-dien-21-oic acid sodium salt Following the procedure of Example 5 and substituting the mercaptans listed in tale II for isopropyl mercaptan, the 16β-thioethers of 3α,11α-dihydroxy-fusida-13(17), 24-dien-21-oic acid sodium salt listed in table I were prepared as mixtures of the two C-20-isomers.

Table II:

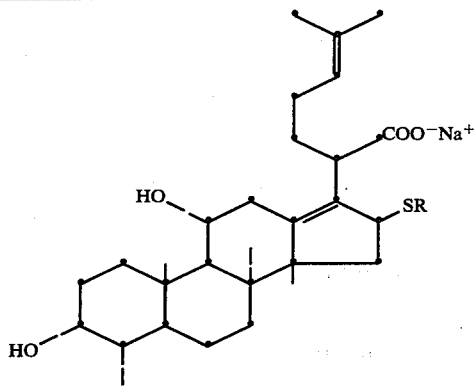

| Example | Mercaptan | Resulting compound R | Mp (° C) |
|---|---|---|---|
| 10 | methyl mercaptan | $CH_3$ | 252–262 |
| 11 | ethyl mercaptan | $CH_2CH_3$ | 201–210 |
| 12 | n-butyl mercaptan | $(CH_2)_3$—$CH_3$ | 136–145 |
| 13 | tert-butyl mercaptan | $C(CH_3)_3$ | 222–235 |
| 14 | allyl mercaptan | $CH_2CH=CH_2$ | 175–200 |
| 15 | cyclohexyl mercaptan | cyclohexyl | > 250 |
| 16 | n-heptyl mercaptan | $(CH_2)_6$—$CH_3$ | 196–210 |
| 17 | n-dodecyl mercaptan | $(CH_2)_{11}$—$CH_3$ | 116–136 |
| 18 | thiophenol | $C_6H_5$ | 243–247 |
| 19 | benzyl mercaptan | $CH_2C_6H_5$ | 210–222 |
| 20 | 2-phenylethyl-mercaptan | $CH_2CH_2C_6H_5$ | 234–242 |
| 21 | 4-tert-butyl-thio-phenol | 4-$C_6H_4C(CH_3)_3$ | 215–225 |
| 22 | thio-2-naphthol | 2-naphthyl | 145–165 |
| 23 | furfuryl mercaptan | 2-furfuryl | 216–221 |
| 24 | 2-pyridyl mercaptan | 2-pyridyl | 216–221 |

EXAMPLE 25

3α,11α-Dihydroxy-16β-isopropylthiofusida-13(17), 24-dien-21-oic acid sodium salt To a solution of 3-O-acetyl-16-deacetoxy-16α-bromofusidic acid benzyl ester (33.5 g, 50 mmol) in 75 ml of dimethylsulfoxide was added a solution of sodium hydroxide (2.4 g, 60 mmol) and isopropyl mercaptan (7 ml, 75 mmol) in 25 ml of ethanol. After stirring at room temperature for 2 hours, 30 per cent aqueous sodium hydroxide (25 ml) was added, and the resulting mixture was heated to 70° C for 2 hours. After cooling to 20° C, water (500 ml), 4-methyl-2-pentanone (500 ml), and 4N aqueous hydrogen chloride (400 ml) were added. The organic phase was collected, washed with water, and filtered. The resulting solution was stirred, while 2N aqueous sodium hydroxide (100 ml) was slowly added causing the desired product to precipitate as colourless crystals. After cooling to 5° C for 2 hours, the crystals were filtered off, washed with water (2 × 10ml) and 4-methyl-2-pentanone (2 × 10ml), and dried to yield analytically pure 3α,11α-dihydroxy-16β-isopropylthiofusida-13(17), 24-dien-21-oic acid sodium salt as a mixture of the two C-20-isomers; melting point 243–248° C.

EXAMPLE 26

3α,11α-Dihydroxy-16β-isopropylthiofusida-13(17)-en-21-oic acid sodium salt

Following the procedure of Example 25 and substituting 3O-acetyl-16-deacetoxy-24,25-dihydro-16α-bromofusidic acid benzyl ester for the corresponding 24,25-unsaturated compound, 3α,11α-dihydroxy-16β-isopropylthiofusida-13(17)-en-21-oic acid was prepared as a crystalline sodium salt; melting point 215°–240° C (dec.).

EXAMPLE 27

3α,11α-Dihydroxy-16β-isopropylthiofusida-13(17),24-dien-21-oic acid

The sodium salt of 3α,11α-dihydroxy-16β-isopropylthiofusida-13(17), 24-dien-21-oic acid (10 g), prepared as described in Example 25, was dissolved in methanol (150 ml), and 1N aqueous hydrochloric acid (17,5 ml) was added. The resulting solution was stirred at 20° C, while 22.5 ml of water was slowly added causing the desired product to crystallize. After stirring for 2 hours, the crystals were filtered off, washed with methanol-water (4/1), and dried to yield 7.0 g of a mixture of the two C-20-isomers of 3α,11α-dihydroxy-16β-isopropylthiofusida-13(17), 24 -dien-21-oic acid, melting point 130°–134° C; $[\alpha]_D^{20}$ = −92.9° (C=1, chloroform). To the mother liquor 10 ml of water was added, causing an additional amount of only one of the two isomers to precipitate as colourless crystals, which were collected and recrystallized from methanol-water to give one of the two C-20-isomeric acids (360 mg) in a pure state, melting point 109°–113° C. $[\alpha]_D^{20}$ = −37.8° (C=1, chloroform).

(This product is identical with that of Example 31C).

EXAMPLE 28

3α,11α-dihydroxy-16β-(2'-aminoethylthio)fusida-13(17),24-dien-21-oic acid

A. 3-Acetyl-16-deacetoxy-16β-(2'-aminoethylthio)fusidic acid benzyl ester

3-Acetyl-16-deacetoxy-16α-bromofusidic acid benzyl ester (2.68 g; 4 mmol) was added to a solution of potassium hydroxide (8.64 g; 130 mmol) and the hydrochloride of cystein amine (9.0 g; 80 mmol) in 150 ml of pure ethanol. After stirring for 16 hours at room temperature, water (200 ml) was slowly added to crystallize the desired compound.

The crystals were filtered off, washed with a mixture of watr (10 ml) and ethanol (10 ml), and dried to yield 3-acetyl-16-deacetoxy-16β-(2'-aminoethylthio)fusidic acid benzyl ester (2.49 g); melting point 150°–173° C.

Recrystallization from methanol-water gave the analytical sample, melting point 184°–186° C.

Found: C 71.61, H 8.92, S 4.81, N 2.04% $C_{40}H_{59}O_5NS$. requires: C 72.15, H 8.93, S 4.81, N 2.10%.

B. 3α,11α-dihydroxy-16β-(2'-aminoethylthio)fusida-13(17),24-dien-21-oic acid 600 mg of the above benzyl ester was dissolved in a mixture of dimethylsulfoxide (50 ml) and 2 N aqueous sodium hydroxide (10 ml). After heating to 70° C for 1.5 hour, water (250 ml) was added. Adjustment of the pH-value to 6.0 by addition of 4 N aqueous hydrochloric acid caused an amorphous product to precipitate. This crude product was filtered off, dried and dissolved in boiling ethyl acetate (150 ml). When this solution was allowed to cool to room temperature with stirring, an amorphous precipitate was formed. The 3α,11α-dihydroxy-16β-(2'-aminoethylthio)fusida-13(17),24-dien-21-oic acid thus obtained was filtered off, and dried to yield a mixture of the two C-20 isomers.

Found: C 65.80, H 9.54, S 5.59, N 2.40% $C_{31}H_{51}NO_4S$. requires: C 65.34, H 9.73, S 5.63, N 2.46%.

The NMR spectrum ($CD_3OD$) shows signals at $\delta$ = 0.96 (d, 3H), 1.01(s, 3H), 1.21 (bs, 6H), 1.59 and 1.65 (2 bs, 6H), 2.5–3.4 (m, 4H; —SC$\underline{H}_2$C$\underline{H}_2$NH$_3^{\oplus}$), 3.61 (m, 1 H; C$\underline{H}$-3), 3.78 (m, 1H; CH-20), 4.31 (m, 1H; C$\underline{H}$-11) and 5.13 (m, 1H; C$\underline{H}$-24) ppm. Tetramethylsilane was used as internal reference.

EXAMPLE 29

3α,11α-dihydroxy-16β-(2'-hydroxyethylthio)fusida-13(17),24-dien-21-oic acid

A. 3-Acetyl-16-deacetoxy-16β-(2'-hydroxyethylthio)fusidic acid benzyl ester

3-Acetyl-16-deacetoxy-16α-bromofusidic acid benzyl ester (1.34 g, 2 mmol) was added to a solution of potassium hydroxide (1.68 g, 25 mmol) and 2-hydroxyethyl mercaptan (2.1 ml. 30 mmol) in 150 ml of pure ethanol. After stirring for 16 hours at room temperature, water (100 ml) was added slowly to crystallize the desired compound. The crystals were filtered off, washed with a mixture of water (5 ml) and methanol (5 ml), and dried to yield 3-acetyl-16-deacetoxy-16β-(2'-hydroxyethylthio)fusidic acid benzyl ester (1.18 g); melting point 167°–176° C.

Recrystallization from methanol-water raised the melting point to 175°–178° C.

B. 3α,11α-dihydroxy-16β-(2'-hydroxyethylthio)-fusida-13(17), 24-dien-21-oic acid 700 mg of the above benzyl ester was dissolved in a mixture of dimethylsulfoxide (50 ml) and 2 N aqueous sodium hydroxide (10 ml). After heating to 70° C for 1.5 hour, the mixture was acidified with 4 N hydrochloric acid (pH=2) and water (100 ml) and ether (100 ml) was added. The organic phase was separated, washed with water (5 × 50 ml), dried, and evaporated in vacuo to give an oily residue, containing the two isomers of the desired product. This residue was separated into two fractions by dry column chromatography on silica gel (cyclohexan:chloroform:acetic acid, 10:80:10).

The more polar of these two fractions separated by dry column chromatography contained one of the two C-20-isomers of 3α,11α-dihydroxy-16β-(2'-hydroxyethylthio)fusida-13(17),24-dien-21-oic acid (290 mg) and the less polar contained 50 mg of the other isomer. The NMR spectrum ($CDCl_3$) of the more polar C-20-isomer shows signals at 1.00(s, 3H), 1.21 (bs, 3H), 1.25 (s, 3H), 1.61 and 1.69 (2 bs, 6H), 2.75 (m, 2H, C$\underline{H}_2$S), 3.5–3.9 (m, 5H, C$\underline{H}$-3, C$\underline{H}$-16, C$\underline{H}$-20 and C$\underline{H}_2$OH), 4.40 (m, 1H, C$\underline{H}$-11) and 5.06 (m, 1H, C$\underline{H}$-24) ppm. Tetramethylsilane was used as internal reference.

The NMR spectrum ($CD_3OD$) of the less polar C-20-isomer shows signals at 0.86 (d, J=7, 3H), 0.97 (s, 3H), 1.13 (s, 3H), 1.20 (s, 3H), 1.56 and 1.61 (2bs, 6H), 2.62 (m, 2H, SC$\underline{H}_2$), 3.5–3.8 (m, 5H, C$\underline{H}$-3, C$\underline{H}$-16, C$\underline{H}$-20 and C$\underline{H}_2$OH), 4.27 (m, C$\underline{H}$-11) and 5.15 (m, 1H, C$\underline{H}$-24) ppm. Tetramethylsilane was used as internal reference.

EXAMPLE 30

Separating the two C-20-isomers of 3α,11α-dihydroxy-16β-phenylthiofusida-13(17),24-dien-21-oic acid A suspension of the sodium salt of 3α,11α-dihydroxy-16β-phenylthiofusida-13(17),24-dien-21-oic acid (1 g of the mixture of isomers prepared according to Example 1) in a mixture of ether (50 ml) and 1 N aqueous hydrochloric acid (10 ml) was shaken until the crystals had disappeared. The organic phase was separated, washed twice with water, dried, and evaporated in vacuo. The residue was dissolved in 5 ml of boiling cyclohexane. Upon cooling to room temperature, a crystalline product separated, which was filtered off, washed with 1 ml of cyclohexane and dried. Recrystallization from 5 ml of cyclohexane yielded one of the two C-20-isomers in a pure state with melting point 96°–98° C.

The mother liquor was evaporated in vacuo and the residue was crystallized from ether-petroleum ether to yield 210 mg of the other C-20-isomer, purified by recrystallization from ether-petroleum ether to show a melting point of 94°–99° C. According to thin layer chromatography (Solvent system: chloroform: cyclohexane:methanol:acetic acid, 80:10:2.5:10; spray reagent: Sulphuric acid) the latter product is the less polar of the two isomers.

EXAMPLE 31

Separating the two C-20-isomers of 3α,11α-dihydroxy-16β-isopropylthiofusida-13(17),24-dien-21-oic acid A. One C-20-isomer of 3α-O-formyl-11α-hydroxy-16β-isopropylthiofusida-13(17),24 -dien-21-oic acid acetoxymethylester The sodium salt of 3α,11α-dihydroxy-16β-isopropylthiofusida-13(17),24-dien-21-oic acid, as prepared in Example 25 (1.5 g, 2.5 mmol) was dissolved in dimethylformamide (15 ml) and chloromethyl acetate (0.3 ml, 3.3 mmol) was added. After standing for 16 hours at 20° C, the reaction mixture was cooled to 0° C and stirred while thionylchloride (1 ml, 13.7 mmol) was slowly added. After stirring for one hour at 20° C ethyl ether (100 ml) was added and the resulting mixture was washed with water (4 × 50 ml), dried and evaporated to yield 1.4 g of a mixture of the two C-20-isomeric esters. This residue was dissolved in petroleum ether (15 ml) and upon scratching one of the two isomers crystallized in a pure state. The crystals were collected, washed with petroleum ether and dried to yield the desired compound, melting point 126°–128° C.

B. The other isomer of 3α-O-formyl-11α-hydroxy-16β-isopropylthiofusida-13(17),24-dien-21-oic acid acetoxymethyl ester.

The mother liquor from the crystallization of the compound of part A of this Example was evaporated in vacuo, and the residue was purified by chromatography on silica gel (cyclohexane:ethyl acetate, 8:2) to give the desired compound as an oily residue.

C. One C-20-isomer of 3α,11α-dihydroxy-16β-isopropylthiofusida-13(17),24-dien-21-oic acid.

The compound of part A of this Example (300 mg) was dissolved in methanol (15 ml), potassium carbonate (300 mg) was added, and the mixture was stirred at room temperature for one hour. The reaction mixture was then evaporated in vacuo and ethyl ether (50 ml) and 1 N hydrochloric acid (25 ml) was added. The organic phase was separated, washed twice with water and evaporated to yield a crude product, which was crystallized from methanol/water to yield one isomer of 3α,11α-dihydroxy-16β-isopropylthiofusida-13(17),24-dien-21-oic acid, melting point 110°–112° C; $[α]_D^{20} = −37.8°$ (C=1 in chloroform).

D. The other C-20-isomer of 3α,11α-dihydroxy-16β-isopropylthiofusida-13(17),24-dien-21-oic acid.

By following the procedure of part C of this Example but substituting the product of part B for that of part A the other isomer of 3α,11α-dihydroxy-16β-isopropyl-thiofusida-13(17),24-dien-21oic acid was prepared as colourless crystals, melting point 144°–140° C; $[α]_D^{20} = −158.7°$ (C=1 in chloroform).

EXAMPLE 32

3α-Hydroxy-11-keto-16β-isopropylthiofusida-13(17),24-dien-21-oic acid

A solution of 3α-O-formyl-11α-hydroxy-16β-isopropylthiofusida-13(17),24-dien-21-oic acid acetoxymethyl ester (300 mg of the isomer described in Example 31 A) in 5 ml of methylene chloride was added to a stirred suspension of pyridinium chlorochromate (600 mg) in 5 ml of methylene chloride. After stirring at room temperature for one hour, ethyl ether (100 ml) was added and the stirring was continued for 30 minutes. Filtration and evaporation afforded 3α-O-formyl-11-keto-16β-isopropylthiofusida-13(17),24-dien-21-oic acid acetoxymethyl ester as an oily residue, which was dissolved in methanol (15 ml). Potassium carbonate (300 mg) was added and the resulting suspension was stirred for one hour at room temperature, and then evaporated in vacuo. Ethyl ether (50 ml) and 1N hydrochloric acid (20 ml) were added to the residue, the organic phase was separated, washed twice with water, dried and evaporated to yield a crude product, which was purified by chromatography on silica gel (Ethyl ether: petroleum ether: acetic acid; 70:30:1/2) to yield 3α-hydroxy-11-keto-16β-isopropylthiofusida-13(17),24-dien-21-oic acid as a colourless foam.

EXAMPLE 33

3-Keto-11α-hydroxy-16β-isopropylthiofusida-13(17),24-dien-21-oic acid.

The sodium salt of 3-keto-16-deacetoxy-16β-isopropylthiofusidic acid (553 mg, 1 mmol) was dissolved in 5 ml of dimethylformamide, and benzyl bromide (0.15 ml, 1.2 mmol) was added. After standing at 20° C for 18 hours, the reaction mixture was diluted with ethyl ether (25 ml), washed with water (4 × 25 ml), dried, and evaporated. The residue, containing the benzyl ester of the starting compound, was dissolved in a mixture of dimethylsulfoxide (20 ml) and 2N aqueous sodium hydroxide (10 ml). After heating for 3 hours at 70° C, ethyl ether (100 ml) and 4N hydrochloric acid (10 ml) were added to the reaction mixture. The organic phase was separated, washed twice with water, dried and evaporated to yield a crude product, which was purified by chromatography on slica gel (cyclohexane:ethyl acetate; 1:1) to yield 3-keto-11α-hydroxy-16β-isopropylthiofusida-13(17),24-dien-21-oic acid as a foam.

EXAMPLE 34

3α,11α-Dihydroxy-16β-phenylthiofusida-13(17),24-dien-21-oic acid acetoxymethyl ester The sodium salt of 3α,11α-dihydroxy-16β-phenylthiofusida-13(17),24-dien-21-oic acid (330 mg, 0.5 mmol; the more polar of the two isomers, as separated in Example 26) was dissolved in 2 ml of dimethylformamide, and chloromethyl acetate (50 μl, 0.55 mmol) was added. After standing at room temperature for 16 hours, ether (50 ml) was added, and the resulting mixture was washed with water (4 × 50 ml), dried, and evaporated to yield 3α,11α-dihydroxy-16β-phenylthiofusida-13(17),24-dien-21-oic acid acetoxymethyl ester (one of the two possible C-20-isomers) as a colourless foam (180 mg).

The NMR spectrum (CDCl$_3$) shows signals at δ= 0.88 (d, J=6, 3H), 0.97 (s, 3H), 1.16 (bs, 6H), 1.59 and 1.67 (2 bs, 6H), 2.02 (s, 3H,

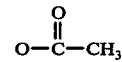

3.52 (m, CH-20), 3.63 (m, CH-3), 4.16 (bd, CH-16), 4.29 (m, CH-11), 5.12 (m, CH-24), 5.67 and 5.81 (2d, J=6,

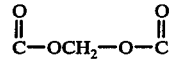

and 7.1–7.5 (5H, aromatic CH) ppm. Tetramethylsilane was used as internal reference.

EXAMPLE 35

3α,11α-Dihydroxy-16β-phenylthiofusida-13(17),24-dien-21-oic acid fusidyloxymethyl ester Following the procedure of Example 34 and substituting fusidic acid chloromethyl ester for chloromethylacetate, 3α,11α-dihydroxy-16β-phenylthiofusida-13(17),24-dien-21-oic acid fusidyloxymethyl ester was prepared as a colourless foam.

EXAMPLE 36

3α,11α-Dihydroxy-16β-methoxyfusida-13(17),24-dien-21oic acid sodium salt

A. 16-Deacetoxy-16β-methoxyfusidic acid benzyl ester

A solution of 16-deacetoxy-16β-methoxyfusidic acid (1.71 g; 3.5 mmol) in methanol (50 ml) was titrated with 2 N methanolic sodium hydroxide using phenolphthalein as an indicator. After evaporation to dryness in vacuo, the amorphous sodium salt thus obtained was dissolved in dimethylformamide (10 ml), benzyl bromide (0.54 ml; 4.5 mmol) was added, and the mixture was stirred at room temperature for 18 hours. Upon dropwise additions of methanol:water 1:1 (30 ml) to the stirred reaction mixture, precipitation of a colourless crystalline product occurred. The crystals were filtered off, washed with methanol:water 1:1, and dried to afford the desired compound, melting point 179°–182° C.

B. 3α,11α-Dihydroxy-16β-methoxyfusida-13(17),24-dien-21-oic acid sodium salt

To a solution of 16-deacetoxy-16β-methoxyfusidic acid benzyl ester (500 mg; 0.86 mmol) in dimethyl sulphoxide (25 ml) was added 2 N aqueous sodium hydroxide (5 ml), and the mixture was stirred at 70° C for 1.5 hours. After cooling to room temperature, water (25 ml) was added dropwise to the stirred reaction mixture whereby a crystalline product precipitated. The crystals were collected, washed with methanol:water 1:1, and dried to yield the sodium salt of 3α,11α-dihydroxy-16β-methoxyfusida-13(17),24-dien-21-oic acid (mixture of C-20 isomers), melting point 224°–228° C (dec.)

Found: C 66.82, H 9.33% $C_{30}H_{47}O_5Na$, 1.5 $H_2O$. requires: C 67.01, H 9.37%.

EXAMPLES 37–39

Additional 3α,11α-dihydroxy-16β-alkyloxyfusida-13(17),24-dien-21-oic acid sodium salts By substituting 16-deacetoxy-16β-ethoxyfusidic acid, 16-deacetoxy-16β-(2'-fluoroethoxy)fusidic acid and 16-deacetoxy-16β-(2',2',2'-trifluoroethoxy)fusidic acid for the 16-deacetoxy-16β-methoxyfusidic acid in the procedure of Example 33, the sodium salts of the 3α,11α-dihydroxy-16β-alkyloxyfusida-13(17),24-dien-21-oic acids (mixtures of C-20 isomers) listed in table III were prepared.

Table III

| Example | R | Mp (° C) |
|---------|---|----------|
| 37 | $CH_2CH_3$ | 216–220 (dec) |
| 38 | $CH_2CH_2F$ | 170–178 (dec) |
| 39 | $CH_2CF_3$ | not determined |

EXAMPLE 40

3α,11α-Dihydroxy-16β-(2',2'2'-trifluoroethoxy)fusida-13(17),24-dien-21-oic acid To a suspension of the sodium salt of 3α,11α-dihydroxy-16β-(2',2',2'-trifluoroethoxy)fusida-13(17),24-dien-21-oic acid (440 mg) in water (15 ml) was added ether (15 ml), and the stirred mixture was acidified with diluted hydrochloric acid. The organic phase was separated, the aqueous phase extracted with ether (10 ml), and the combined ethereal extracts washed twice with water, dried and evaporated in vacuo to yield the desired compound (mixture of C-20 isomers, ratio:approximately 1:1) as a colourless foam.

The above residue was crystallized from ether, the crystals were collected and recrystallized twice from the same solvent to give one of the two C-20 isomeric acids in a pure state, melting point 173°–174° C. According to thin layer chromatography (solvent system: Chloroform:cyclohexane:methanol:acetic acid 80:10:2.5:10; spray reagent: Sulphuric acid) the crystalline compound was the more polar C-20 isomer.

Found: C 66.74, H 8.56%, $C_{31}H_{47}F_3O_5$. requires: C 66.89, H 8.51%.

EXAMPLES 41–43

Additional pure C-20 isomers of 3α,11α-dihydroxy-16β-alkyloxyfusida-13(17),24-dien-21-oic acids Following the procedure of Example 40, but substituting the sodium salt of 3α,11α-dihydroxy-16β-methoxyfusida-13(17), 24-dien-21-oic acid and the sodium salts of the corresponding 16β-ethoxy and 16β-(2'-fluoroethoxy) derivatives for the sodium 3α,11α-dihydroxy-16β-(2',2',2'-trifluoroethoxy)fusida-13(17),24-diene-21-oate, one of the pure C-20 isomers of the 3α,11α-dihydroxy-16β-alkyloxyfusida-13(17),24-dien-21-oic acids listed in table IV were obtained.

Table IV

| Example | R | Mp (° C) |
|---------|---|----------|
| 41 | $CH_3$ | 163–164 |
| 42 | $CH_2CH_3$ | 175–177 |
| 43 | $CH_2CH_2F$ | 172–173 |

EXAMPLE 44

In vitro bactericidal effect of 3α,11α-dihydroxy-16β-phenylthiofusida-13(17),24-dien-21-oic acid compared to that of fusidic acid To two tubes containing NIH broth was added:
a. The sodium salt of 3α,11α-dihydroxy-16β-phenylthiofusida-13(17),24-dien-21-oic acid (10 μg/ml)
b. The sodium salt of fusidic acid (10 μg/ml)

The tubes were inoculated with Streptococcus pyogenes to give $9.2 \times 10^4$ organisms per ml, incubated at 37° C, and the viable counts were determined at intervals.

A third tube was treated similarly without addition of any of the antibiotics and used as a control:

| Tube | Viable count after | | | |
|------|------|------|------|------|
| | 0 hr | 1.5 hr | 4 hr | 7 hr |
| a | $9.2 \times 10^4$ | $1.4 \times 10^4$ | $5.7 \times 10^2$ | $5 \times 10$ |
| b | $9.2 \times 10^4$ | $1.2 \times 10^5$ | $1.5 \times 10^5$ | $1.3 \times 10^5$ |
| control | $9.2 \times 10^4$ | $6.8 \times 10^5$ | $2.4 \times 10^7$ | $1.7 \times 10^8$ |

EXAMPLE 45

In vitro-effect of the combination of fusidic acid and 3α,11α-dihydroxy-16β-isopropylthio-fusida-13(17),24-dien-21-oic acid To 3 tubes containing NIH broth was added:

a. The sodium salt of fusidic acid (1 μg/ml).

b. The sodium salt of 3α,11α-dihydroxy-16-isopropylthiofusida-13(17),24-dien-21-oic acid (3 μg/ml).

c. A mixture of the sodium salts of fusidic acid (1 μg/ml) and 3α,11α-dihydroxy-16-isopropylthiofusida-13(17),24-dien-21-oic acid (3 μg/ml).

The tubes were inoculated with Staphylococcus aureus to give $1.4 \times 10^4$ organisms per ml, incubated at 37° C for 24 hours, and the viable counts were determined.

A fourth tube was treated similarly without addition of any of the antibiotics and used as a control:

| Tube | Viable count |
| --- | --- |
| a | $1.8 \times 10^8$ |
| b | $1.5 \times 10^6$ |
| c | $7.3 \times 10^8$ |
| control | $6.2 \times 10^8$ |

The surviving organisms in tube a are resistant to fusidic acid, and those in tube b are resistant to 3α,11α-dihydroxy-16β-isopropylthio-fusida-13(17),24-dien-21-oic acid, whereas the combination of the two compounds in tube c prevents development of resistance.

EXAMPLE 46

In vitro-effect of the combination of dihydro-fusidic acid and 3α,11α-dihydroxy-16β-phenylthio-fusida-13(17),24-dien-21-oic acid To three tubes containing NIH broth was added:

a. The sodium salt of dihydro-fusidic acid (10 μg/ml).

b. The sodium salt of 3α,11α-dihydroxy-16-phenylthiofusida-13(17),24-dien-21-oic acid (10 μg/ml).

c. A mixture of the sodium salts of dihydro-fusidic acid (5 μg/ml) and 3α,11α-dihydroxy-16-phenylthiofusida-13(17),24-dien-21-oic acid (5 μg/ml).

The tubes were inoculated with Staphylococcus aureus to give $5.2 \times 10^5$ organisms per ml, incubated at 37° C for 96 hours, and the viable counts were determined.

A fourth tube was treated similarly without addition of any of the antibiotics and used as a control:

| | Viable counts after | | | | |
| --- | --- | --- | --- | --- | --- |
| | 0 | 2 | 6½ | 24 | 96 hours |
| Control | $5.2 \times 10^5$ | $1.3 \times 10^6$ | $4.6 \times 10^7$ | $4.3 \times 10^8$ | full growth |
| a | | $4.1 \times 10^5$ | $3.1 \times 10^5$ | $6.3 \times 10^6$ | " |
| b | | $5.2 \times 10^4$ | $1.1 \times 10^4$ | $3.1 \times 10^6$ | " |
| c | | $1.5 \times 10^5$ | $4.1 \times 10^4$ | <10 | <10 |

The surviving organisms in tube a are resistant to dihydro-fusidic acid, and those in tube b are resistant to 3α,11α-dihydroxy-16β-phenylthio-fusida-13(17),24-dien-21-oic acid, whereas the combination of the two compounds in tube c prevents development of resistance.

EXAMPLE 47

Prevention of development of resistance against fusidic acid as a result of treating Staph. aureus with the sodium salt of 3α,11α-dihydroxy-16β-isopropylthiofusida-13(17),24-dien-21-oic acid After a 48 hours pretreatment of a fusidic acid sensitive strain of Staph. aureus (Leo CC 178B) with subinhibitory concentrations of fusidic acid or the compound of Example 9. The sensitivities of the pretreated cultures and of the original strain against the two compounds were determined. The determinations were made by serial dilutions in NIH-broth, inoculum size $2.10^5$ organisms/ml, and read as $IC_{50}$ after 18 and 48 hours. The results can be seen in the following Table B:

Table B

| | $IC_{50}$ in μg/ml | | | |
| --- | --- | --- | --- | --- |
| | 18 hours | | 48 hours | |
| Isolates from | Fusidic acid | Compound of Ex 9 | Fusidic acid | Compound of Ex 9 |
| Control culture | 0.016 | 2 | 1 | 5 |
| Fusidic acid cult. | 7.9 | 1.6 | 50 | 5 |
| Comp. of Ex 8 cult. | 0.016 | 5 | 0.020 | 16 |

The emergence of resistance of the control culture against fusidic acid as seen by the increased $IC_{50}$-values after 48 hours is further increased by the pretreatment with fusidic acid.

Only a slight decrease of the sensitivity to the compound of Example 9 is seen. Pretreatment with fusidic acid did not influence the results.

Pretreatment of the culture with the compound of Example 9 totally prohibited the emergence of resistance against fusidic acid.

EXAMPLE 48

In vitro activity of 3α,11α-dihydroxy-16β-ethylthiofusida-13(17),24-dien-21-oic acid against Staph. aureus before and after a number of transfers.

Serial dilutions of the compound above were made in liquid NIH-medium and then heavily inoculated with either a fusidic acid sensitive strain of Staph. aureus (Leo CC 178B) or with a fusidic acid resistant variant of the same strain (Leo CC 178A).

After every 72 to 96 hours transfers were made from the tubes containing the largest amount of the test compound showing full growth. The table below shows the sensitivities read after overnight incubation.

Table C

| Stph. aureus | $IC_{50}$ in μg/ml | | | | | | |
| --- | --- | --- | --- | --- | --- | --- | --- |
| | before | and after a certain member of transfer | | | | | |
| | | 1st | 2nd | 3rd | 4th | 5th | 6th |
| Leo CC 178B (fusidic acid sensitive) | 2.7 | 2.0 | 7.4 | 7.4 | 13.5 | 10.0 | 32 |
| Leo CC 178A (fusidic acid resistant) | 2.7 | 2.3 | 3.8 | 4.3 | 4.2 | 4.0 | 4.0 |

It will be seen from the table that the fusidic acid sensitive strain shows a 12 fold decrease of sensitivity to the compound in question after the 6th transfer, whereas the fusidic acid resistant strain hardly shows any change in sensitivity. This is a highly unexpected phenomenon.

EXAMPLE 49

| Cream | |
| --- | --- |
| 3α,11α-dihydroxy-16β-isopropylthiofusida-13(17),24-dien-21-oic acid | 20 g |
| Petrolatum | 150 g |
| Liquid paraffin | 150 g |
| Spermaceti | 50 g |
| Sorbitan monopalmitate | 50 g |
| Polyoxyethylene sorbitan monopalmitate | 50 g |
| Water | 530 g |

EXAMPLE 49—continued

| Cream | |
|---|---|
| | 1000 g |

Heat petrolatum, paraffin, spermaceti, sorbitanmonopalmitate, and polyoxyethylene sorbitan monopalmitate to 70° C. and add slowly the water at 72° C with agitation. Continue agitation until the cream has cooled. Triturate 3α,11α-dihydroxy-16β-isopropylthiofusida-13(17),24-dien-21-oic acid into the cream base and homogenize using a roller mill. Fill the cream into laquered aluminium collapsible tubes.

EXAMPLE 50

| Ointment | |
|---|---|
| 3α,11α-dihydroxy-16β-ethylthiofusida-13(17),24-dien-21-oic acid sodium salt | 20 g |
| Liquid parafffin | 138 g |
| Cetanol | 4 g |
| Lanolin anhydrous | 46 g |
| Petrolatum | 792 g |
| | 1000 g. |

Melt paraffin, cetanol, lanolin, and petrolatum at 70° C. After cooling to below 40° C, triturate 3α,11α-dihydroxy-16β-ethylthiofusida-13(17),24-dien-21-oic acid sodium salt. Fill the ointment into laquered collapsible aluminium tubes.

EXAMPLE 51

| Capsule | |
|---|---|
| 3α,11α-dihydroxy-16β-isopropylthio-fusida-13(17)-en-21-oic acid sodium salt | 250 g |
| Microcrystalline cellulose | 145 g |
| Magnesium stearate | 5 g |
| | 400 g |

Pass the ingredients through a 60 mesh sieve and mix for 10 minutes. Fill the mixture into hard gelatin capsules No. 00 (Parke Davis & Co.) using a capsule fil weight of 400 mg.

EXAMPLE 52

| Preparation of tablets | |
|---|---|
| 3α,11α-dihydroxy-16β-isopropylthiofusida-13(17),24-dien-21-oic acid | 250 g |
| Avicel PH 101 | 120 g |
| STA-Rx 1500 | 120 g |
| Magnesium stearate | 10 g |

3α,11α-dihydroxy-16β-isopropylthiofusida-13(17), 24-dien-21-oic acid, Avicel and STA-Rx are mixed together, sieved through a 0.7 mm sieve and thereafter mixed with the magnesium stearate. The mixture is pressed into tablets each of 500 mg.

EXAMPLE 53

| Preparation of suspension | |
|---|---|
| 3α,11α-dihydroxy-16β-phenylthiofusida-13(17),24-dien-21-oic acid | 5.00 g |
| Citric acid | 0.45 g |
| Sodium monohydrogenphosphate | 0.70 g |
| Sucrose | 25.00 g |
| Tween 80 | 0.05 g |
| Potassium sorbate | 0.20 g |
| Carboxymethylcellulose-Na | 0.50 g |
| Purified water | qs to 100 ml suspension |

The crystals are micronized and suspended in a solution of the citric acid, the sodium monohydrogenphosphate, the sucrose, the potassium sorbate and the Tween 80 in 50 ml water, if necessary under slight warming. The carboxymethylcellulose-Na is dissolved in 20 ml of boiling water. After cooling, it is added to the other ingredients. The suspension is homogenized in a blender and finally purified water is added to a total volume of 100 ml.

EXAMPLE 54

| Cream | |
|---|---|
| 3α,11α-Dihydroxy-16β-isopropylthiofusida-13(17),24-dien-21-oic acid (A) | 10 g |
| 16-Deacetoxy-16β-ethyloxyfusidic acid (B) | 10 g |
| Petrolatum | 150 g |
| Liquid paraffin | 150 g |
| Spermaceti | 50 g |
| Sorbitan monopalmitate | 50 g |
| Polyoxyethylene sorbitan monopalmitate | 50 g |
| Water | 530 g |
| | 1000 g |

Heat petroleum, paraffin, spermaceti, sorbitanmonopalmitate, and polyoxyethylene sorbitan monopalmitate to 70° C and add slowly the water at 72° C with agitation. Continue agitation until the cream has cooled. Triturate A and B into the cream base and homogenize using a roller mill. Fill the cream int laquered aluminium collapsible tubes.

EXAMPLE 55

| Ointment | |
|---|---|
| 16-Deacetoxy-16β-isopropylsulphinyl fusidic acid sodium salt ($A_2$) | 2.5 g |
| 3α,11α-dihydroxy-16β-isopropylthio-fusida-13(17),24-dien-21-oic acid sodium salt ($B_2$) | 7.5 g |
| Liquid paraffin | 138 g |
| Cetanol | 4 g |
| Lanolin anhydrous | 46 g |
| Petrolatum | 802 g |
| | 1000 g |

Melt paraffin, cetanol, lanolin, and petrolatum at 70° C. After cooling to below 40° C, triturate $A_2$ and $B_2$. Fill the ointment into laquered collapsible tubes.

EXAMPLE 56

| Capsule | |
|---|---|
| Fusidic acid sodium salt | 125 g |
| 3α,11α-dihydroxy-16β-ethylthiofusida-13(17),24-dien-21-oic acid sodium salt | 125 g |
| Microcrystalline cellulose | 145 g |
| Magnesium stearate | 5 g |
| | 400 g |

Pass the ingredients through a 60 mesh sieve and mix for 10 minutes. Fill the mixture into hard gelatin capsules No. 00 (Parke Davis & Co.) using a capsule fil weight of 400 mg.

EXAMPLE 57

| Ointment | |
|---|---|
| Fusidic acid sodium salt (A) | 10 g |
| 3α,11α-dihydroxy-16β-phenylthiofusida--13(17),24-dien-21-oic acid sodium salt (B) | 10 g |
| Liquid paraffin | 138 g |
| Cetanol | 4 g |
| Lanolin anhydrous | 46 g |
| Petrolatum | 792 g |
| | 1000 g |

Melt paraffin, cetanol, lanolin, and petrolatum at 70° C. After cooling to below 40° C, triturate A and B. Fill the ointment into laquered collapsible aluminium tubes.

EXAMPLE 58

| Cream | |
|---|---|
| Fusidic acid ($A_1$) | 5 g |
| 3α,11α-dihydroxy-16β-phenylthiofusida-13(17),24-dien-21-oic acid ($B_1$) | 15 g |
| Petrolatum | 150 g |
| Liquid paraffin | 150 g |
| Spermaceti | 50 g |
| Sorbitan monopalmitate | 50 g |
| Polyoxyethylene sorbitan monopalmitate | 50 g |
| Water | 530 g |
| | 1000 g |

Heat petrolatum, paraffin, spermaceti, sorbitan-monopalmitate, and polyoxyethylene sorbitan monopalmitate to 70° C and add slowly the water at 72° C with agitation. Continue agitation until the cream has cooled. Triturate $A_1$ and $B_1$ into the cream base and homogenize using a roller mill.

Fill the cream into laquered aluminium collapsible tubes.

What we claim is:

1. A compound of the formula I:

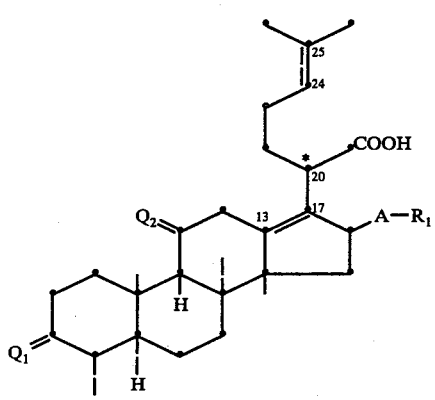

in which formula the dotted line between C-24 and C-25 indicates that the carbon atoms in question are connected by either a double bond or a single bond, and the asterix at C-20 indicates that the compounds exist in two diastereomeric forms; and in which formula $Q_1$ and $Q_2$ stand for the group

or oxygen, A represents oxygen or sulphur, and $R_1$ stands for a straight or branched, unsubstituted or substituted alkyl radical having from 1 to 12 carbon atoms, an alkenyl radical having from 3 to 6 carbon atoms, a cycloalkyl radical having from 3 to 7 carbon atoms in the alicyclic ring, an unsubstituted or halo- or lower alkyl-substituted phenyl-lower alkyl or phenyl radical; a naphthyl radical; or a heterocyclic radical having 5 or 6 ring atoms and containing one oxygen, sulphur or nitrogen atom; the pure diastereomers of the compounds of formula I and mixtures thereof, and pharmaceutically acceptable non-toxic salts and easily hydrolysable esters of the compounds of formula I.

2. A compound of the formula I of claim 1 in which $Q_1$ and $Q_2$ stand for the group

or oxygen, A represents oxygen or sulphur, and $R_1$ stands for a straight or branched, unsubstituted or with hydroxy, amino or halogen substituted alkyl radical having from 1 to 12 carbon atoms, an alkenyl radical having from 3 to 4 carbon atoms, a cyclohexyl radical, an unsubstituted or with halogen or lower alkyl substituted phenyl radical, a phenyl-lower alkyl radical, a naphthyl radical, or a furfuryl or pyridyl radical; the pure diastereomers of the compounds of formula I and mixtures thereof, and pharmaceutically acceptable non-toxic salts or easily hydrolysable esters of the compounds of formula I.

3. A compound of the formula I of claim 1 in which A stands for oxygen.

4. A compound of the formula I of claim 1 in which A stands for sulphur.

5. A compound of the formula I of claim 1 in which $Q_1$ stands for oxygen.

6. A compound of the formula I of claim 1 in which $Q_2$ stands for oxygen.

7. A compound of the formula I of claim 1 in which $Q_1$ and $Q_2$ stand for the group

8. A compound of formula I of claim 1 in which the bond between C-24 and C-25 is a double bond.

9. A compound of formula I of claim 1 in which the bond between C-24 and C-25 is a single bond.

10. A compound of the formula I of claim 1 in which $R_1$ stands for an alkyl radical substituted with a member selected from the group consisting of halogen, hydroxy, and amino.

11. A compound of the formula I of claim 1, in which $R_1$ stands for phenyl-lower alkyl or phenyl radical substituted with one or two members selected from the group consisting of halogen, and lower alkyl.

12. 3α,11α-Dihydroxy-16β-phenylthiofusida-13(17),24-dien-21-oic acid, and pharmaceutically acceptable, non-toxic salts or easily esters hydrolysable thereof as defined in claim 1.

13. 3α,11α-Dihydroxy-16β-(4'-bromophenylthio)-fusida-13(17),24-dien-21-oic acid, and pharmaceutically acceptable, non-toxic salts or easily esters hydrolysable thereof as defined in claim 1.

14. 3α,11α-Dihydroxy-16β-isopropylthiofusida-13(17), 24-dien-21-oic acid, and pharmaceutically acceptable, non-toxic salts or easily esters hydrolysable as defined in claim 1.

15. 3α,11α-Dihydroxy-16β-tert-butylthiofusida-13(17), 24-dien-21-oic acid, pharmaceutically acceptable, non-toxic or satls and easily esters hydrolysable thereof as defined in claim 1.

16. 3α,11α-Dihydroxy-16β-allylthiofusida-13(17),24-diene-21-oic acid, and pharmaceutically acceptable, non-toxic salts or easily esters hydrolysable thereof as defined in claim 1.

17. 3α,11α-Dihydroxy-16β-furfurylthiofusida-13(17),24-dien-21-oic acid, and pharmaceutically acceptable, non-toxic salts or easily esters hydrolysable thereof as defined in claim 1.

18. 3α,11α-Dihydroxy-16β-ethythiofusida-13(17), 24-dien-21-oic acid, and pharmaceutically acceptable, non-toxic salts or easily esters hydrolysable thereof as defined in claim 1.

19. 3α,11α-Dihydroxy-16β-isopropylthiofusida-13(17)-en-21-oic acid, and pharmaceutically acceptable, non-toxic salts or easily esters hydrolysable thereof as defined in claim 1.

20. 3α,11α-Dihydroxy-16β-phenylthiofusida-13(17)-en-21-oic acid, and pharmaceutically acceptable, non-toxic salts or easily esters hydrolysable thereof as defined in claim 1.

21. The pure isomers of the acid of claim 12.

22. The pure isomers of the acid of claim 14.

23. Method for producing a compound of formula I of claim 1, in which a compound of formula II, in which formula $Q_1'$ stands for $Q_1$ as defined above or for $R_3$ representing an alkanoyl, an aralkanoyl or an aroyl radical; $R_1$, A, $Q_2$ and the dotted line between C-24 and C-25 have the meaning as defined above; and $R_2$ represents a benzyl radical or a substituted benzyl radical, is reacted with an inorganic or organic base in the presence of an organic solvent to form a compound of formula I, which is recovered in the form of an acid, or salt or an easily hydrolysable ester as defined in claim 1.

24. Method for separating the two possible C-20-isomers of a compound of formula I of claim 1, in which a mixture of the two pure isomers is subjected to a fractionate crystallization.

25. Method of claim 24, in which the separation is performed by chromatography.

26. A pharmaceutical preparation in dosage unit form for the enteral or parenteral treatment of patients suffering from bacterial infectious diseases, which comprises as an active ingredient at least one compound of formula I, or a pharmaceutically acceptable, non-toxic salt or an easily hydrolysable ester thereof, and an atoxic pharmaceutically acceptable carrier, the quantity of the said active compound being between 0.05 g and 1 g.

27. A preparation as claimed in claim 26 wherein the dosage unit contains from 0.25 g to 0.75 g of at least one compound of formula I or a salt or ester thereof as defined in claim 1.

28. A preparation as claimed in claim 26 wherein the dosage unit is in the form of a tablet.

29. A preparation as claimed in claim 26 wherein the dosage unit is in the form of a capsule.

30. A parenteral pharmaceutical preparation in dosage unit form, containing from 0.05 g to 1 g of at least one compound of formula I of claim 1 or a salt or ester thereof as defined in claim 1 as dry matter, in an ampoule, vial or other suitable receptacle, for reconstitution.

31. A preparation according to claim 26, dissolved or suspendend in a non-toxic, pharmaceutically acceptable vehicle.

32. A pharmaceutical preparation for oral treatment in form of a sustained-release preparation in dosage unit form of at least one compound of claim 1, in which the dose of the active compound is between 0.05 g to 1 g.

33. A preparation for oral treatment in the form of a suspension of at least one compound of formula I as such or of a sparingly soluble salt or ester, said preparation containing from 20 to 100 mg per ml of a non-aqueous vehicle.

34. A preparation for topical treatment in the form of a powder or an ointment or cream containing at least one compound of formula I or a salt or ester as defined in claim 1 in an amount of from ½ g to 10 g per 100 g of the preparation 35. A preparation according to claim 26 in which the dosage unit additionally contains an antibiotic selected from the group consisting of fusidic acid, fusidic acid derivatives, β-lactam antibiotics, tetracyclines, rifamycins, erythromycin, lycomycin, and clindamycin.

36. A preparation according to claim 35 which in addition to at least one compound of formula I or a salt or an ester thereof as defined in claim 1 contains a penicillanic acid antibiotic.

37. A preparation according to claim 35 which in addition to at least one compound of formula I or a salt or an ester thereof as defined in claim 1 contains a cephalosporanic acid antibiotic.

38. A preparation according to claim 35 which in addition to at least one compound of formula I or a salt or an ester thereof as defined in claim 1 contains a fusidic acid antibiotic different from a compound of formula I of claim 1.

39. A preparation according to claim 35 which in addition to at least one compound of formula I or a salt or an ester thereof as defined in claim 1 contains a tetracycline antibiotic.

40. A method of treating patients suffering from bacterial infectious diseases, comprising administering to (adult) patients from 0.25 to 100 mg per day of at least one compound of formula I of claim 1 or an equivalent amount of a salt or ester thereof as defined in claim 1.

41. A method according to claim 40, in which a preparation according to claim 26 is used.

42. A method of treating patients suffering from bacterial infectious diseases, comprising administering to adult patients from 0.25 to 100 mg per day of a preparation according to claim 27.

43. A method of treating patients suffering from bacterial infectious diseases, comprising administering to adult patients from 0.25 to 100 mg per day of a preparation according to claim 28.

44. A method of treating patients suffering from bacterial infectious diseases, comprising administering to adult patients from 0.25 to 100 mg per day of a preparation according to claim 29.

45. A method of treating patients suffering from bacterial infectious diseases, comprising administering to adult patients from 0.25 to 100 mg per day of a preparation according to claim 30.

46. A method of treating patients suffering from bacterial infectious diseases, comprising administering to adult patients from 0.25 to 100 mg per day of a preparation according to claim 31.

47. A method of treating patients suffering from bacterial infectious diseases, comprising administering to adult patients from 0.25 to 100 mg per day of a preparation according to claim 32.

48. A method of treating patients suffering from bacterial infectious diseases, comprising administering to adult patients from 0.25 to 100 mg per day of a preparation according to claim 33.

49. A method of treating patients suffering from bacterial infectious diseases, comprising administering to adult patients from 0.25 to 100 mg per day of a preparation according to claim 34.

50. A method of treating patients suffering from bacterial infectious diseases, comprising administering to adult patients from 0.25 to 100 mg per day of a preparation according to claim 35.

51. A method of treating patients suffering from bacterial infectious diseases, comprising administering to adult patients from 0.25 to 100 mg per day of a preparation according to claim 36.

52. A method of treating patients suffering from bacterial infectious diseases, comprising administering to adult patients from 0.25 to 100 mg per day of a preparation according to claim 37.

53. A method of treating patients suffering from bacterial infectious diseases,, comprising administering to adult patients from 0.25 to 100 mg per day of a preparation according to claim 38.

* * * * *